US006270962B1

(12) United States Patent
Chamberlin et al.

(10) Patent No.: US 6,270,962 B1
(45) Date of Patent: Aug. 7, 2001

(54) METHODS FOR THE ELIMINATION OF DNA SEQUENCING ARTIFACTS

(75) Inventors: Michael Chamberlin, Kensington; Daniel Mytelka, Berkeley, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/687,591

(22) PCT Filed: Jan. 30, 1995

(86) PCT No.: PCT/US95/01200

§ 371 Date: Feb. 2, 1998

§ 102(e) Date: Feb. 2, 1998

(87) PCT Pub. No.: WO95/20682

PCT Pub. Date: Aug. 3, 1995

(51) Int. Cl.$^7$ .................. C12Q 1/68; C12P 19/34
(52) U.S. Cl. .................. 435/6; 435/91.2
(58) Field of Search ................... 435/6, 91.2

(56) References Cited

U.S. PATENT DOCUMENTS 5,545,539   8/1996   Miller ..................... 435/91.2

FOREIGN PATENT DOCUMENTS 44 11 588 C1   9/1995   (DK) .
WO 96/12041    4/1996   (WO) .

OTHER PUBLICATIONS

Baskaran, Namadev, et al., *Genome Research*, 6:633–638 (1996).
Del Sal, Giannino, et al., *BioTechniques*, 7(5):514–519 (1989).
Melchior, William B., et al., *Proc. Nat. Acad. Sci. USA*, 70(2):298–302 (1973).
Pisa–Williamson, Denise, et al., U.S. Biochemical Corp. (Editorial Comments), 19(2):29–36 (1992).
Rees, William A., et al., *Biochemistry*, 32:137–144 (1993).
Sanger, F., et al., *Proc. Natl. Acad. Sci. USA*, 74:5463–5467 (1977).
Santoro, Marcelo M., et al., *Biochemistry*, 31:5278–5283 (1992).
Winship, P.R., "An improved method for directly sequencing PCR amplified material using dimethyl sulphoxide," *Nucleic Acids Research*, 17(3):1266 (1989).
Thakar, M. et al., "Osmolyte Mediation of T7 DNA Polymerase and Plasmid DNA Stability," *Biochemistry*, 33:12255–12259 (1994).

*Primary Examiner*—Eggerton A. Campbell
(74) *Attorney, Agent, or Firm*—Quarles & Brady LLP; Gregory T. Pletta (57) ABSTRACT

The present invention relates to improvements in methods of DNA sequencing. In particular, the invention relates to the elimination of stops or pauses in chain termination methods of DNA sequencing by the addition of nitrogen-containing organic compounds such as betaine, trimethylamine N-oxide and dimethylglycine. The invention also provides for DNA sequencing kits containing these compounds. The invention also provides for improvements in other laboratory procedures using DNA polymerases, such as polymerase chain reaction (PCR).

63 Claims, 1 Drawing Sheet

FIG. 1.

METHODS FOR THE ELIMINATION OF DNA SEQUENCING ARTIFACTS

This invention was made with Government support under Grant (Contract) No. GM12010 awarded by the National Institutes of Health (NIH). The Government has certain rights to this invention.

BACKGROUND OF THE INVENTION

The present invention relates primarily to improvements in methods of DNA sequencing. In particular, the invention relates primarily to the elimination of stops or pauses in chain termination methods of DNA sequencing by the addition of nitrogen-containing organic compounds such as betaine, trimethylamine N-oxide and dimethylglycine. The invention also provides for DNA sequencing kits containing these compounds. The invention also provides for improvements in other laboratory procedures using DNA polymerases, such as polymerase chain reaction (PCR).

Efficient DNA sequencing technology is very important to the development of the biotechnology industry as well as for basic biological research. Improvements in both efficiency and accuracy of DNA sequencing are needed to keep pace with the demands for DNA sequence information. The Human Genome Project, for example, has set a goal for dramatically increasing the efficiency, cost-effectiveness and throughput of DNA sequencing techniques. (See Collins, F., and Galas, D. (1993) *Science* 262:43–46.)

Most DNA sequencing today is carried out by a chain termination method of DNA sequencing. The most popular chain termination methods are variants of the dideoxynucleotide-mediated chain termination method of Sanger (see Sanger et al. (1977) *Proc. Nat. Acad. Sci., USA* 74:5463–5467). Thousands of laboratories employ this technique including those doing automated sequencing for the Human Genome Project. Commercial kits containing the reagents needed for this method of DNA sequencing are available and are widely used.

Although commonly used, the Sanger (dideoxy) sequencing technique has problems and limitations. One of the major problems with this method is the incidence of DNA polymerase stops or pauses which interfere with the determination of the DNA sequence. Stops are predominantly problematic in regions of the DNA that are GC-rich or in regions that are especially far from the primer. In addition, stops occur more frequently in impure DNA preparations. Because of this, DNA purification is generally required before DNA can be sequenced by the dideoxy method.

Various methods have been proposed to eliminate stops in dideoxy sequencing. For example, researchers have tried varying the reaction temperature, using a variety of DNA polymerases, stabilizing the DNA polymerase, and extending the prematurely terminated DNA molecules with terminal deoxynucleotidyl transferase (see T. W. Fawcette and S. G. Bartlett (1990) *BioTechniques* 9:46–48; D. Pisa-Williamson and C. W. Fuller (1992) United States Biochemical Corp. Comments 19:29–36; J. Sambrook, E. F. Fritsch and T. Maniatis, ed. (1989) *Molecular Cloning: A Laboratory Manual*, second edition, Cold Spring Harbor Press, Cold Spring Harbor, N.Y.; and F. M. Ausubel, R. Brent, R. E. Kingston, D. D. Moore, J. G. Seidman, J. A. Smith and K. Struhl, ed. (1989) *Current Protocols in Molecular Biology*, Greene Publishing Associates and Wiley-Interscientific, John Wiley and Sons, N.Y.) However, none of these methods has been reliable. There is a continuing need to eliminate the problem of stops in DNA sequencing and thereby improve the efficiency and cost-effectiveness of this important process.

SUMMARY OF THE INVENTION

This invention provides for methods of decreasing the incidence of DNA polymerase stops that occur in a reaction mixture containing a DNA polymerase. The incidence of DNA polymerase stops is decreased by the addition of nitrogen-containing organic molecules, which are described herein, to the reaction mixture. These compositions of the invention are added to the reaction mixture in an amount that is effective to decrease the incidence of DNA polymerase stops. The reaction mixture can be used in a chain termination method of DNA sequencing. Preferably the chain termination method of DNA sequencing is a dideoxynucleotide DNA sequencing method. The reaction mixture can also be a PCR reaction mixture. The DNA which is sequenced or amplified can be purified or unpurified. Unpurified DNA can be present, for example, as a crude cell lysate.

The method of decreasing the incidence of DNA polymerase stops can be combining, in an aqueous solution, a DNA molecule, a DNA polymerase or DNA polymerases, a mixture of deoxyribonucleoside triphosphates, a chain elongation inhibitor, and one or more of the compositions of the invention to form a reaction mixture. The DNA polymerase is capable of producing a nucleic acid complementary to a portion of the DNA molecule by using the DNA molecule as a template. The reaction mixture is incubated to allow the DNA polymerase to form nucleic acid fragments of varying length by using the DNA molecule as a template. The nucleic acid fragments that are formed are complementary to the DNA molecule that is being sequenced.

In some variations of the above method, a nucleic acid primer is also added to the reaction mixture. This primer is complementary to a second portion of one strand of the DNA molecule that is located downstream from the first portion of that strand. The DNA polymerase that is used is capable of extending the 3' end of the primer to produce a nucleic acid that is complementary to the first portion of the DNA molecule.

The invention provides improved methods for sequencing a DNA molecule by the chain termination method, wherein the DNA molecule is combined with a DNA polymerase capable of producing a nucleic acid complementary to a portion of the DNA molecule by using the DNA molecule as a template; with a mixture of deoxyribonucleoside triphosphates; and with chain elongation inhibitor, to form a reaction mixture. This reaction mixture is incubated to permit the DNA polymerase to form nucleic acid fragments of varying length by using the DNA molecule as a template, wherein the nucleic acid fragments are complementary to the DNA molecule. The improved part of this method is the addition to the reaction mixture of an amount of one or more of the nitrogen-containing organic compounds described herein.

The invention also provides for kits for DNA sequencing by the chain termination method. These kits have instructional material, a container which contains one or more deoxyribonucleoside triphosphates, a container which contains a chain elongation inhibitor, and an amount of the compositions of the invention. The kits may also contain other components. Preferably, the kits are for DNA sequencing by the dideoxy DNA sequencing method.

BRIEF DESCRIPTION OF THE DRAWINGS

FIG. 1A. DNA polymerase stops in dideoxy DNA sequencing. Dideoxy DNA sequencing of double-stranded DNA was carried out as described in example 1 herein, except that water was substituted for betaine (results were identical with or without water). The reaction mixture was separated on a polyacrylamide/urea DNA sequencing gel as described in example 1. The positions of DNA polymerase stops are shown by arrows.

FIG. 1B. Elimination of DNA polymerase stops in dideoxy DNA sequencing by betaine. Dideoxy DNA sequencing was carried out in the presence of betaine as described in example 1. The reaction mixture was separated on a polyacrylamide/urea DNA sequencing gel as described in example 1. The arrows show the positions corresponding to the DNA polymerase stops of FIG. 1A.

DEFINITIONS

The term "nucleic acids", as used herein, refers to either DNA or RNA. It includes plasmids, infectious polymers of DNA and/or RNA, nonfunctional DNA or RNA, chromosomal DNA or RNA and DNA or RNA synthesized in vitro (such as by the polymerase chain reaction). "Nucleic acid sequence" or "polynucleotide sequence" refers to a single- or double-stranded polymer of deoxyribonucleotide or ribonucleotide bases read from the 5' to the 3' end.

The term "DNA molecule" as used herein refers to DNA molecules in any form, including naturally occurring, recombinant, or synthetic DNA molecules. The term includes plasmids, bacterial and viral DNA as well as chromosomal DNA. The term encompasses DNA fragments produced by cell lysis or subsequent manipulation of DNA molecules. Unless specified otherwise, the left hand end of single-stranded DNA sequences is the 5' end.

The term "upstream" when used in respect to a single stranded DNA molecule, refers to those DNA sequences located 5' to a reference region of the DNA molecule. For example, those sequences located upstream from a defined portion of a DNA molecule are those located 5' to the defined portion. Similarly, the term "downstream", when used with respect to single stranded DNA molecule, refers to those DNA sequences located 3' to a reference region of the DNA molecule.

The term "complementary" as used herein refers to a relationship between two nucleic acid sequences. One nucleic acid sequence is complementary to a second nucleic acid sequence if it is capable of forming a duplex with the second nucleic acid, wherein each residue of the duplex forms a guanosine-cytidine (G-C) or adenosine-thymidine (A-T) basepair or an equivalent basepair. Equivalent basepairs can include nucleoside or nucleotide analogues other than guanosine, cytidine, adenosine, or thymidine, which are capable of being incorporated into a nucleic acid by a DNA or RNA polymerase on a DNA template. A complementary DNA sequence can be predicted from a known sequence by the normal basepairing rules of the DNA double helix (see Watson J. D., et al. (1987) *Molecular Biology of the Gene*, Fourth Edition, Benjamin Cummings Publishing Company, Menlo Park, Calif., pp. 65–93). Complementary nucleic acids may be of different sizes. For example, a smaller nucleic acid may be complementary to a portion of a larger nucleic acid.

The term "DNA template" or "template" as used herein, refers to a DNA molecule or portion of a DNA molecule that is used by a DNA or RNA polymerase to determine the sequence of a newly synthesized nucleic acid. (See Watson, J. D., et al., supra for a detailed description of the action of DNA and RNA polymerases on template DNA molecules).

The term "replicating", as used herein in reference to a DNA polymerase, refers to the process of using a DNA molecule as a template to produce a nucleic acid complementary to a portion of the DNA molecule.

The terms "purified DNA" or "purified DNA molecule," as used herein, refers to DNA that is not contaminated by other biological macromolecules, such as RNA or proteins, or by cellular metabolites. Purified DNA contains less than 5% contamination (by weight) from protein, other cellular nucleic acids and cellular metabolites. The terms "unpurified DNA" or "unpurified DNA molecules" refer to preparations of DNA that have greater than 5% contamination from other cellular nucleic acids, cellular proteins and cellular metabolites. Unpurified DNA may be obtained by using a single purification step, such as precipitation with ethanol combined with either LiCl or polyethylene glycol. The term "crude cell lysate preparation" or "crude cell lysate" or "crude lysate" refers to an unpurified DNA preparation where cells or viral particles have been lysed but where there has been no further purification of the DNA.

Some compounds of the invention may be present with a positive or negative charge or with both a positive and negative charges, depending on the pH of the solution. It is understood that these various forms of these compounds are included in the present invention.

The term betaine, as used herein, refers to N,N,N-trimethylglycine.

All numerical ranges in this specification are intended to be inclusive of their upper and lower limits.

DETAILED DESCRIPTION

A. Introduction

There are a number of different methods of determining the sequence of DNA molecules. Most methods in common use today are variations on one of two general methods. One general scheme uses chemical reagents which react with specific bases to allow other chemicals to cleave the phosphodiester backbone at those points. The second general method uses a polymerase enzyme to produce DNA fragments complementary to the DNA molecule to be sequenced. The inclusion of low amounts of chain elongation inhibitors in the reaction mixture causes different sized DNA fragments to be generated. The DNA fragments generated by either chemical methods or chain termination methods can be separated and analyzed by a variety of methods. For example, they can be separated on a sequencing gel based on size. By examining the bands present at any position on the gel, the sequence of the DNA molecule can be determined at the corresponding position. For example, the top of the sequence noted in FIG. 1A contains three consecutive G nucleotides, since bands are present at that position in only the G lane.

Chain termination methods of DNA sequencing are much more widely used than chemical cleavage methods. Dideoxynucleoside triphosphates are the most common chain terminators used in DNA sequencing. For examples of specific protocols for dideoxy DNA sequencing, see Sambrook, et al., supra.

In spite of its wide use, there are technical problems associated with the dideoxy sequencing method. One of the major problems is the incidence of stops or pauses of the DNA polymerase which interfere with the determination of the DNA sequence. When the DNA polymerase stops at a particular site, bands appear in all four lanes of the sequencing gel, and the nucleotide residue at that position cannot be determined.

DNA polymerase stops occur for several reasons. Stops are observed more frequently as the enzyme extends farther from the 3' end of the primer. This phenomenon limits the length of DNA fragment that can sequenced at one time. Reducing the incidence of stops allows longer pieces of DNA to be sequenced and therefore makes DNA sequencing more efficient.

DNA polymerase stops also occur more frequently when contaminants are present in the DNA preparation. Because of this phenomenon, DNA preparations must be purified prior to sequencing. The improved DNA sequencing method of the invention decreases the incidence of stops and therefore allows less pure preparations of DNA to be reliably sequenced. This, in turn, increases the efficiency and reduces the cost of DNA sequencing.

Lastly, even under optimal conditions, DNA polymerase stops are often seen in GC-rich regions of the DNA. This makes DNA sequence information in certain areas of a DNA molecule difficult to determine. This problem is, of course, compounded when one is trying to determine a DNA sequence in a GC-rich region far from the 3' end of the primer or in a DNA preparation that has not been optimally purified. Thus, the improved method of the invention increases the accuracy and efficiency of DNA sequencing while reducing its cost.

The reduced incidence of DNA polymerase stops caused by the compounds of the invention also has utility in procedures other than DNA sequencing. Numerous common laboratory techniques, such as PCR (polymerase chain reaction), in vitro mutagenesis, nick translation, reverse transcription and blunt ending utilize DNA polymerases. The addition of appropriate concentrations of the compounds of the invention can potentially increase the efficiency or speed of these procedures.

B. Compounds That Reduce the Incidence of DNA Polymerase Stops

The compounds used in the present invention are nitrogen-containing organic molecules that are capable of eliminating or reducing the incidence of stops occurring in chain-termination methods of DNA sequencing and in other laboratory procedures using DNA polymerases, such as PCR. These compounds are represented by the formula:

(I)

wherein:

$R^1$, $R^2$, and $R^3$ may be the same or different and are independently selected from the group consisting of hydrogen, methyl, ethyl, and propyl, with the proviso that no more than two of $R^1$, $R^2$, and $R^3$ are hydrogen; and X is a moiety selected from the group consisting of:
radicals of the formulas
(a)=O; and (b)

wherein:

$R^4$ is selected from the group consisting of methyl, hydrogen and, when combined with $R^1$, forms a pyrrolidine ring;

$R^5$ is selected from the group consisting of —$CO_2H$ and —$SO_3H$; and n is an integer of from 0 to 2; and with the proviso that, when $R^1$ and $R^4$ form a pyrrolidine ring, no more than one of $R^2$ and $R^3$ is hydrogen, and wherein the composition is added in an amount effective to decrease the incidence of stops.

When a pyrrolidine ring is formed by $R^1$ and $R^{4'}$ a compound of formula II is formed.

(II)

In certain preferred embodiments, the methods and kits of this invention use compounds of formula I wherein $R^1$, $R^2$ and $R^3$ are the same or different and selected from the group consisting of methyl, ethyl and hydrogen with the proviso that no more than two of $R^1$, $R^2$ and $R^3$ are hydrogen and, when $R^1$ and $R^4$ form a pyrrolidine ring, no more than one of $R^2$ and $R^3$ are hydrogen.

In another group of preferred embodiments, the methods and kits of this invention use a compound of formula I wherein X is —$CH_2CO_2H$. Further preferred embodiments within this group use compounds where $R^1$, $R^2$ and $R^3$ are methyl; where $R^1$, $R^2$ are methyl and $R^3$ is hydrogen; or where $R^1$ is methyl and $R^2$ and $R^3$ are hydrogen.

In further preferred embodiments, the methods and kits of this invention use a compound of formula I wherein X is =O and $R^1$, $R^2$ and $R^3$ are methyl.

In still further preferred embodiments, the methods and kits of this invention use a compound of formula I wherein $R^1$ and $R^4$ form a pyrrolidine ring, $R^2$ and $R^3$ are methyl, n is 0, and $R^5$ is —$CO_2H$ (stachydrine, formula III).

(III)

In yet another group of preferred embodiments, the methods and kits of this invention use compounds wherein $R^1$, $R^2$, and $R^3$ are methyl and X is —$CH_2$—$SO_3H$ (sulfobetaine).

In general, the compounds used to eliminate or reduce the incidence of DNA polymerase stops in DNA sequencing and in other laboratory procedures using a DNA polymerase are commercially available. For example, betaine, dimethylglycine, sarcosine, and trimethylamine N-oxide can all be obtained from Sigma Chemical Company (St. Louis, Mo., USA).

These compounds may also be synthesized by routine methods known to those of skill in the art. For example, compounds of formula wherein $R^4$ is H, n is 0 and $R^5$ is —$CO_2H$ can be synthesized by the method of Lloyd, et al. (1992) *J. Pharm. Pharmacol.* 44:507–511. In general, ethyl chloroacetate is heated to reflux with the appropriate tertiary amine in ethanol. When the reaction is complete, the ethanol is removed from the reaction mixture by evaporation under reduced pressure. The residue is dissolved in 3–6% w/v aqueous HCl and warmed to reflux. Evaporation of the solvent under reduced pressure provides the desired products. Typically, these products can be recrystallized from an acetonitrile/water mixture.

Compounds of formula I wherein $R^4$ is H or $CH_3$, n is 1 and $R^5$ is $CO_2H$ can be synthesized by the method of Fiedorek, F. T., U.S. Pat. No. 2,548,428. In brief, betalactones are reacted with tertiary amines to provide the desired compounds.

Compounds of formula I wherein $R^4$ is H, n is 2, and $R^5$ is —$CO_2H$ can be synthesized by the method of Aksnes, G., et al. *J. Chem. Soc. London* 1959:103–107. In brief, 4-bromobutyric acid (Aldrich Chemical Co., Milwaukee, Wis., USA) is converted to a methyl ester by treatment with methyl alcohol and catalytic sulfuric acid. Subsequent treatment of the methyl ester with excess alcoholic tertiary amine provides the desired compounds.

Compounds of formula I wherein $R^4$ and $R^1$ are taken together to form a pyrrolidine ring and where $R^5$ is $CO_2H$ are synthesized by the general method of Karer, et al. (1925) *Helv. Chim. Acta.* 8:364. For example, stachydrine is formed by the methylation of proline, according to this procedure.

Compounds of formula I wherein X is =O are synthesized by oxidation of the corresponding tertiary amines (see March, J. (1992) *Advanced Organic Chemistry, Reactions, Mechanisms and Structure*, Fourth Edition, John Wiley and Sons, New York, pp. 1200–1201). Typically, the oxidation is carried out with hydrogen peroxide, but other peracids may also be used.

Sulfobetaine can be synthesized according to the procedure of King, J. F., et al. (1985) *J. Phosphorus Sulfur* 25:11–20. Other compounds of formula I wherein $R^5$ is —$SO_3H$ can also be synthesized by modifications of this procedure and by other methods known to those of skill in the art.

C. Improved Methods for DNA Sequencing, Polymerase Chain Reaction and Other Laboratory Procedures Using DNA Polymerases 1. Chain Termination Methods of DNA Sequencing The present invention encompasses an improvement in DNA sequencing by the chain termination method. As used herein, the terms "chain termination method of DNA sequencing," "chain termination method" or "chain termination DNA sequencing method" refer to a DNA sequencing method that uses a DNA polymerase to produce nucleic acid fragments complementary to a portion of the DNA molecule to be sequenced. Generally, a primer is used that is complementary to a portion of the DNA molecule. The primer is extended along the DNA molecule template by the DNA polymerase. The principle of the method is that low amounts of specific chain elongation inhibitors are included in the reaction mixture so that the DNA polymerase will only occasionally incorporate an inhibitor and terminate. Generally, four reaction mixtures are set up, each with a different chain elongation inhibitor, capable of specifically terminating at a guanosine, cytosine, adenosine or thymidine residue. The DNA fragments generated by incubation with the DNA polymerase can be separated and analyzed to determine the sequence of the DNA molecule. Typically, the fragments are separated by gel electrophoresis and detected by autoradiography, although other separation or detection methods may also be used. (See Sanger, et al., supra and Sambrook, et al., supra, for a more detailed description of the chain termination method of DNA sequencing.) This procedure is amenable to automation, and various specific methods have been created for that purpose, including single lane sequencing, laser detection and capillary electrophoresis.

The terms "chain elongation inhibitors" or "chain-terminating inhibitors", as used herein, refer to compounds that terminate nucleic acid chain elongation by a DNA polymerase enzyme. As described above, these compounds may be useful in chain termination methods of DNA sequencing.

The terms "pause", "stop", "DNA polymerase pause" or "DNA polymerase stop" as used herein refer to a phenomenon wherein the DNA polymerase stops or does not function at a particular nucleotide when the DNA polymerase is incubated with DNA in a chain terminating DNA sequencing method. This is a phenomenon in which DNA polymerase molecules fail to continue elongation despite the presence of the next nucleotide to be incorporated and the absence of any manifest reason why elongation should cease (such as the incorporation of a dideoxynucleotide). When the DNA fragments are displayed on a DNA sequencing gel, stops appear as bands in all four lanes of the gel at a position corresponding to the length of the fragment that the DNA polymerase molecules had difficulty elongating, so the identity of the nucleotide at that position cannot be determined (see arrows in FIG. 1A for examples).

There are a variety of different chain termination methods for sequencing DNA. The most commonly used method is the dideoxynucleotide DNA sequencing method. The terms "dideoxynucleotide DNA sequencing method" or "dideoxy DNA sequencing method", as used herein, refer to a chain termination method of DNA sequencing wherein the chain elongation inhibitors are 2'3'-dideoxynucleosides or their derivatives. Typically, 2'3'-dideoxynucleoside triphosphates are used. A variety of other chain elongation inhibitors may also be used. For example, arabinonucleoside derivatives or 3' O-methyl deoxyribonucleotide derivatives may be used in chain termination methods. (See Sanger, et al., supra and Axelrod, V. O., et al. (1978) *N.A.R.* 5:3549–3563.)

A variety of different enzymes can be used to produce DNA fragments complementary to the DNA molecule to be sequenced. For example, T7 DNA polymerase, Taq polymerase, and the Klenow fragment of DNA polymerase I are all used in DNA sequencing. RNA polymerase and reverse transcriptase have also been used. DNA polymerases may be genetically or physically altered to optimize the enzyme for use in DNA sequencing.

The DNA polymerases require a primer sequence. The primer sequences may be generated by digestion of the DNA molecule or may be added exogenously as a primer molecule. The terms "primer molecule", "primer" or "nucleic acid primer" or "DNA primer", as used herein, refer to a single-stranded nucleic acid molecule which is complementary to a portion of the DNA molecule to be sequenced. Primers are allowed to anneal to a DNA molecule, so that subsequent elongation of the 3' end of the primer by a DNA polymerase produces a nucleic acid sequence complementary to a portion of the DNA molecule to be sequenced. Primers are commonly used in chain termination methods of DNA sequencing. However, in certain modifications of DNA sequencing by the chain termination method, primer sequences may be generated by digestion with appropriate enzymes (see below).

In an alternative embodiment, DNA sequencing vectors may be used to facilitate DNA sequencing by chain termination methods. A variety of such vectors may be used, including M13, Bluescript vectors such as pBS-KS$^+$and pBS-KS$^-$ (Stratagene, San Diego, Calif., U.S.A.), pUC vectors such as pUC18 and pUC19 and pBR322 vectors. The DNA molecule to be sequenced is inserted into the sequencing vector. Primers can be constructed that are complementary to a region of the DNA in the sequencing vector, so that elongation from the 3' end of the primer will produce DNA fragments complementary to portions of the DNA molecule to be sequenced. Thus, when sequencing vectors are used, the DNA molecule to be sequenced can be present as an insert in the vector. Primers that are complementary to a region of the DNA sequencing vector can be used, so that chain elongation occurs from the 3' end of the primer into the region of the DNA insert, thereby allowing determination of the DNA sequence of the insert.

The DNA preparation for sequencing may be either purified or unpurified. Unpurified DNA may be a crude cell lysate. The compounds of the invention that eliminate or reduce the incidence of DNA polymerase stops allow for the use in DNA sequencing of unpurified DNA preparations, including crude cell lysates.

The DNA preparation may be present in single-stranded or double-stranded form. For instance, linear double-stranded DNA may be generated by PCR. When such DNA is sequenced, the incidence of DNA polymerase stops is reduced or eliminated.

The mixture of DNA fragments generated in chain termination methods of DNA sequencing is most commonly separated and analyzed by gel electrophoresis. See FIGS. 1A and 1B herein for an example of a DNA sequencing gel. Other separation methods useful for separating DNA fragments may also be used (see Sambrook, et al., supra). For instance, mass spectrometry can be used to analyze mixtures of DNA fragments (see Jacobson, et al. (1991) *J. Genetic Analysis, Techniques and Applications* 8:223–229.

The DNA fragments may be labeled or unlabeled. For example, unlabeled DNA fragments may be detected by ultraviolet spectroscopy in an automated technique or by silver staining after gel electrophoresis. However, it is generally desirable to produce labeled DNA fragments to facilitate their detection. For instance, radiolabeled DNA fragments may be produced. They may be produced, for example, by use of a radioactive primer. Alternatively, radioactive nucleotides may be incorporated during the incubation with a DNA polymerase. When radiolabeled DNA fragments are produced, they may be separated by gel electrophoresis and visualized by autoradiography (see FIGS. 1A and 1B, herein). A wide variety of non-radioactive labels may also be used including fluorophores, chemiluminescent agents and small detectable molecules, such as biotin. For example, in automated sequencing techniques, fluorescent or calorimetric labels can be detected by laser spectroscopy using capillary tubes or sequencing gels.

Non-radioactive labels may be attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labelled, naturally occurring anti-ligands. Alternatively, any haptenic or antigenic compound can be used in combination with an antibody.

There are a variety of modifications of the chain termination method of DNA sequencing. For example, DNA sequencing may be performed manually, by semi-automated procedures or by the use of an automated DNA sequencing instrument. In addition, chain termination DNA sequencing technology may be combined with other techniques. For example, in "exometh" methods, a DNA molecule is treated with exonuclease to generate a series of DNA molecules with single-stranded 5' extensions of varying length. These DNA molecules can then be sequenced directly by a chain termination method of DNA sequencing without the addition of an exogenous primer. (See Sorge, J. A., et al. (1989) *Proc. Nat. Acad. Sci, USA* 86: 9208–9212 for a more detailed description of DNA sequencing by the "exometh" modification.) Such modifications of chain termination DNA sequencing methods are all encompassed by the present invention.

The compounds of the invention may be added to the reaction mixture before or during the incubation of the DNA with the DNA polymerase to eliminate or reduce the incidence of stops. The order of addition of the DNA molecule, the DNA polymerase, the chain elongation inhibitors, the deoxyribonucleoside triphosphates, the primer, and the compounds of the invention may also be varied. As demonstrated in Example 4, the compounds that reduce or eliminate the incidence of stops may even be added after the normal incubation time for the DNA polymerase, and the incubation may be extended to remove DNA polymerase stops.

2. Polymerase Chain Reaction Procedures

The present invention also encompasses an improvement in nucleic acid amplification procedures, such as PCR, which involve chain elongation by a DNA polymerase.

There are a variety of different PCR techniques which utilize DNA polymerase enzymes, such as Taq polymerase. See *PCR Protocols: A Guide to Methods and Applications*. (Innis, M, Gelfand, D., Sninsky, J. and White, T., eds.), Academic Press, San Diego (1990) for detailed description of PCR methodology. In a typical PCR protocol, a target nucleic acid, two oligonucleotide primers (one of which anneals to each strand), nucleotides, polymerase and appropriate salts are mixed and the temperature is cycled to allow the primers to anneal to the template, the polymerase to elongate the primer, and the template strand to separate from the newly synthesized strand. Subsequent rounds of temperature cycling allow exponential amplification of the region between the primers. The primers can anneal to both the original template and the newly synthesized nucleic acid, as long as the polymerase is able to extend at least as far as the position to which the other primer anneals. For this reason, the ability of PCR to amplify a product is primarily limited by the ability of the polymerase to extend the annealed primer. The ability of the polymerase to extend the annealed primer is dependent on the distance between the primers and the nucleotide composition of the sequence between them. The addition of an appropriate amount of one or more of the compounds described herein facilitates this elongation. See example 8 and example 9, herein, for a demonstration of the effects of betaine on chain elongation in PCR protocols using Taq polymerase. Other compounds of the invention in addition to betaine can be used in a similar manner to improve chain elongation in a variety of different PCR methods.

The compounds of the invention also have utility in reducing DNA polymerase stops in laboratory procedures other than DNA sequencing and polymerase chain reactions. Numerous common laboratory techniques, such as in vitro mutagenesis, nick translation, reverse transcription and blunt ending utilize DNA polymerases. See Sambrook, et al. (1989) *Molecular Cloning: A Laboratory Manual*, second edition, Vol. 1–3, Cold Spring Harbor Press, Cold Spring Harbor, N.Y. (1989) for a description of these methods. Thus, the compounds of the invention are useful in a variety of procedures involving chain elongation by a DNA polymerase.

3. Testing and Optimization of Compounds That Reduce or Eliminate the Incidence of Stops Compounds capable of eliminating or reducing the incidence of stops in chain termination methods of DNA sequencing and in other laboratory procedures using DNA polymerase are described above. These compounds may be tested for their relative ability to eliminate or reduce DNA polymerase stops. For instance, the compounds may be tested by the procedure described in Example 1, herein. Briefly, DNA sequencing is carried out by a dideoxy sequencing method in the presence or absence of a selected concentration of a compound of the invention. The DNA sequencing gels obtained in the presence and absence of the compound are then compared to determine the effectiveness of the compound in eliminating DNA polymerase stops (see for example, FIGS. 1A and 1B). Effective concentrations for each of the compounds may be determined by this procedure. Optimal concentrations for a given compound may vary for the different variations of chain termination DNA sequencing methods. These concentrations may be readily determined experimentally by adding different amounts of a compound and determining the incidence of stops (see for instance, Example 7, herein).

This invention also encompasses kits for DNA sequencing by the chain termination method which comprise an amount of one or more of the compounds described herein that eliminate or reduce the incidence of DNA polymerase stops. The kits may further comprise instructional material, a container which contains one or more deoxyribonucleoside triphosphates, a container which contains a DNA polymerase, and a container that contains a chain elongation inhibitor. The containers in the kit may be combined in various ways. For example, a chain elongation inhibitor may be combined in the same container with the mixture of deoxyribonucleoside triphosphates.

This invention also encompasses kits for DNA polymerase chain reaction which comprise an amount of one or more of the compounds described herein that eliminate or reduce the incidence of DNA polymerase stops. The kits may further comprise instructional material, a container which contains a DNA polymerase, and a container that contains deoxyribonucleoside triphosphates.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

EXAMPLES

Example 1

Elimination of Stops in a Dideoxy Method of DNA Sequencing by Betaine

Betaine eliminates stops that are routinely observed in a standard dideoxy sequencing procedure.

Betaine monohydrate was obtained from Sigma and stored as a 5.5M stock solution at −20° C. Modified T7 polymerase (Sequenase 2.0 (Amersham, Arlington Heights, Ill., U.S.A.)) and nucleotide mixes were purchased from USB. $^{35}$S-dATP was purchased from Amersham.

DNA sequencing generally followed the protocol of Del Sal et al. (1989) *BioTechniques* 7:514–519. Sequencing was performed by mixing 1 picomole (pmole) of supercoiled double stranded plasmid DNA (purified by running over a QIAGEN tip-100 column according to the manufacturer's specifications) with 2–4 pmole of various oligonucleotide primers (generally purified by polyacrylamide gel electrophoresis, though this proved unnecessary for primers under 30 nucleotides) and adjusting the volume to 10 μl containing 0.1 N NaOH. The tube was incubated for ten minutes at 68° C., then it was moved to room temperature and 4 μl of TDMN (200 mM NaCl, 50 mM DTT, 120 mM HCl, 80 mM $MgCl_2$, 280 mM TES) were added. After a further ten minute incubation at room temperature, 2 μl of GTP labeling mix (7.5 μM dCTP, 7.5 μM dGTP, 7.5 μM dTTP) and 5 μCi of $^{35}$S-dATP were added, followed by 2 μl of Sequenase (diluted 1:8 in cold 10 mM Tris.Cl pH 8.0, 1 mM EDTA). This mix was incubated for five minutes at room temperature, then 3.5 μl were aliquoted to each of four tubes preheated to 37° C., each containing 3.5 μl of 5.5 M betaine and 2.5 μl of one of the termination mixes (80 μM each dNTP, 8 μM one ddNTP, 50 mM NaCl), for a final concentration of approximately 2M betaine. This was incubated for five minutes at 37° C., then stopped with 4 μl of stop solution (80% deionized formamide, 1×TBE, 0.05% xylene cyanol, 0.05% bromophenol blue.) After 2.5 minutes at 95° C., the tubes were briefly chilled on ice. 4.5 μl were loaded on a 6% polyacrylamide (19:1 acrylamide: bisacrylamide)/7M urea/1×TBE gel, which was run for various periods at 35 W. The gels were fixed with a 12% methanol/12% acetic acid solution, transferred to Whatman paper, and dried. They were generally exposed overnight on Kodak XAR 5 film.

Figure 1:
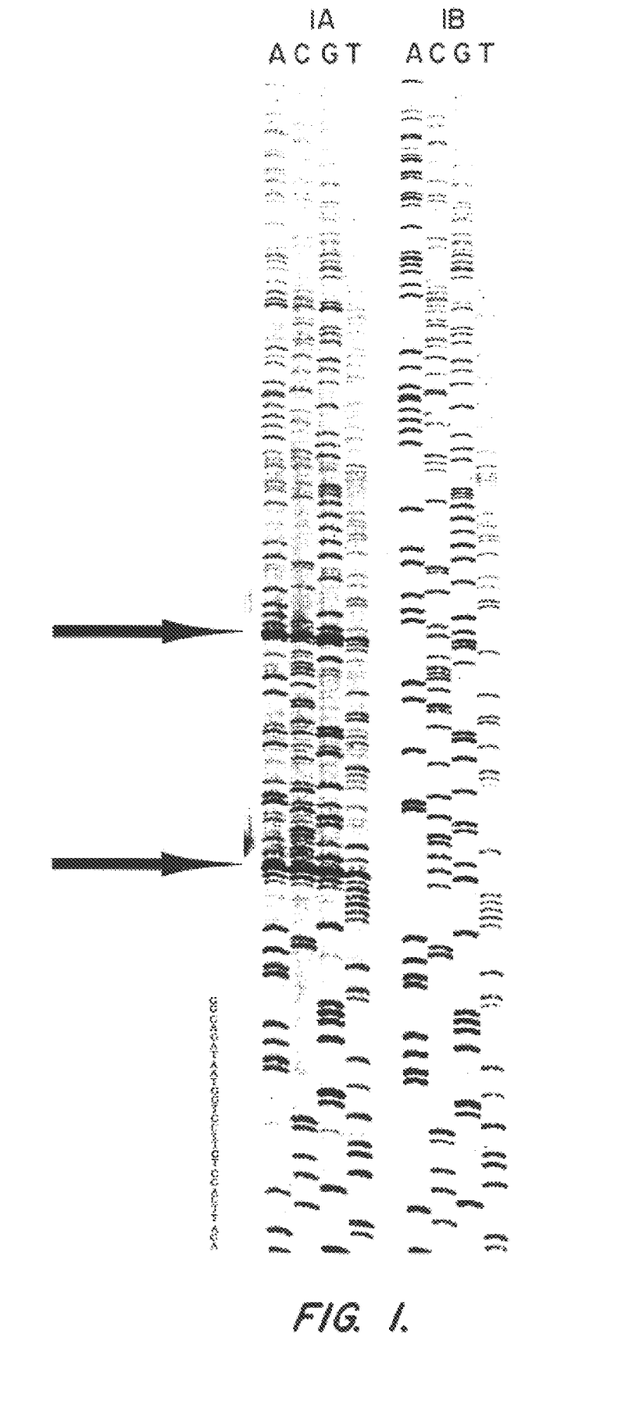

The addition of betaine at a concentration of 2M eliminated virtually all stops when DNA sequencing was performed using a modified form of the method of Del Sal et al., supra, as described above. Sequencing without betaine leads to occasional stops, which tend to occur in GC-rich regions and in regions particularly far from the primer (FIG. 1A). An analysis of seventeen such stops indicates that they tend to occur after the middle position of sequences similar to pyrimidine-guanine-cytosine, with eleven of seventeen stops examined matching this consensus and the other six differing at only one position. There was no obvious correlation with potential secondary structure of the single stranded template, as determined by the program MFOLD, part of the GCG package. In the presence of betaine (FIG. 1B), all of these stops disappear, allowing the correct sequence to be determined.

Example 2

Readable DNA Sequences Farther from a Primer are Obtained in the Presence of Betaine The incidence of stops in DNA sequencing by the dideoxy method increases in regions of the DNA located farther from the primer. This phenomenon limits the useful DNA sequence that can be obtained from one primer. However, the inclusion of betaine in the dideoxy sequencing reaction mixture decreases the incidence of stops in DNA regions far downstream from the primer. This allows useful sequence information to be obtained in these regions of the DNA without doing an additional sequencing reaction with another primer.

DNA sequencing was performed in the presence and absence of 2M betaine as described in example 1. The resulting sequencing reactions were run on a DNA sequencing gel as described in example 1, except that the gel was run for 12 hours to examine longer DNA fragments. These longer DNA fragments clearly showed the sequence of DNA regions farther from the primer than those routinely obtained in dideoxy DNA sequencing procedures. Little useful sequence information could be determined from these gels in the absence of betaine. However, in the presence of betaine, DNA sequence could be read up to at least 520 nucleotides from the 3' end of the primer, with sequences beyond that becoming less readable because of the resolving power of the gel.

Example 3
DNA Sequence Determination from Unpurified DNA Preparations in the Presence of Betaine DNA was prepared generally following a standard alkaline lysis technique (See Silhavy et al. (1984) *Experiments With Gene Fusions*, Cold Spring Harbor Laboratory, Cold Spring Harbor, N.Y. 147–148), followed by an ethanol precipitation. No organic extraction, RNAse treatment or other further purification technique was used. XL1-blue cells (Stratagene, San Diego, Calif.) containing the pDSM3 plasmid were used as a source of the DNA. The DNA was then sequenced as described for example 1. As expected, there were a large number of stops in the absence of betaine. However, the stops present while sequencing this DNA disappeared when betaine was added to the termination reaction.

Example 4
Elimination of Stops During DNA Sequencing by Chasing with Betaine

Betaine is capable of eliminating stops when added after the normal termination reaction. DNA sequencing was carried out as described in example 1, except that no betaine was added with the termination mixture. After the 5 minute incubation at 37° C., either 3.5 µl of 5.5 betaine solution or 3.5 µl of water was added. The incubation was then continued for an additional 5 minutes and was stopped with stop solution as in example 1. Addition of betaine at this point greatly reduced the stops observed in the absence of betaine. Thus, the bands representing stops on the sequencing gels appear to represent halted DNA polymerase complexes. Betaine, added after the normal incubation with the termination mixes, is capable of allowing the halted DNA polymerase complexes to resume elongation. This demonstrates that betaine is not simply acting by stabilizing the DNA polymerase, since its addition at this point would have no effect if that were the case.

Example 5
Elimination or Reduction of the Incidence of Stops in Modified Dideoxy DNA Sequencing Procedures The DNA sequencing procedure of example 1 was altered to demonstrate that betaine is able to eliminate stops that occur in a variety of dideoxy DNA sequencing protocols. The effect of substituting a single-stranded DNA substrate or using different DNA polymerases in a dideoxy DNA sequencing procedure was examined.

a) Sequencing of Single-Stranded DNA

Single stranded DNA was prepared from strain XL1-blue containing plasmid pDSM6, according to routine procedures. When single stranded DNA was sequenced by the procedure described in example 1, fewer stops were observed in the absence of betaine than in double-stranded specimens. However, these stops were also eliminated by betaine.

b) Sequencing Using Klenow DNA Polymerase Enzyme

DNA sequencing was carried out essentially by the procedure described in example 1, except that the Klenow fragment of *E. coli* DNA polymerase was used. 7.5 units of the Klenow enzyme was used and the extension mix was modified to include 20 µCi of $^{35}$S-dATP and 0.1 µl of DTT in addition to the GTP extension mix. Stops were observed in different places with the use of the Klenow enzyme but were generally eliminated by betaine, just as described above for the procedure using Sequenase.

c) Sequencing Using Taq Polymerase Enzyme

DNA sequencing was carried out according to the Promega "fmol™ DNA Sequencing System" protocol (Promega Corporation, Madison, Wis., USA). The protocol is described below.

(1) End label primer.

(2) Mix 4–40 fmol DNA template, 5 µl 5×fmol sequencing buffer (250 mM Tris.Cl pH 9.0, 10 mM MgCl2), 1.5 pmole labeled primer, betaine and water to a final volume of 16 µl containing an appropriate concentration of betaine (e.g., 2M).

(3) Add 1 µl sequencing Grade Taq DNA Polymerase (5 U/µl)

(4) Add 4 µl of the above to each of the dNTP/ddNTP mixes according to the following table:

|  | A | C | G | T |
| --- | --- | --- | --- | --- |
| dATP | 20 µM | 20 µM | 20 µM | 20 µM |
| dCTP | 20 µM | 20 µM | 20 µM | 20 µM |
| 7 Deaza dGTP | 20 µM | 20 µM | 20 µM | 20 µM |
| dTTP | 20 µM | 20 µM | 20 µM | 20 µM |
| ddATP | 350 µM | — | — | — |
| ddCTP | — | 200 µM | — | — |
| ddGTP | — | — | 30 µM | — |
| ddTTP | — | — | — | 600 µM |

(5) overlay with one drop of mineral oil.

(6) Place tubes in thermal cycler preheated to 95° C.

(7) Start appropriate cycling program (varies with primer, one example is 95° C. for 2 minutes, 30 cycles of (95° C. for 30 sec., 42° C./30 sec., 70°/60 sec.)).

(8) Add 3 µl stop solution (10 mM NaOH, 95% formamide, 0.05% bromophenol blue, 0.05% xylene cyanol).

(9) Heat at 95° C. for 2½ minutes, ice quench, and load on a sequencing gel.

Sequencing gels were run and the presence of DNA polymerase stops was determined as described in Example 1, herein. The incidence of stops observed in the reaction mixture was reduced in the presence of betaine.

Example 6
Elimination of Stops During DNA Sequencing by Dimethylglycine, sarcosine (monomethylglycine) and trimethylamine N-oxide (TMANO)

Three additional compounds were demonstrated to decrease the incidence of stops in a dideoxy DNA sequencing procedure. Dimethylglycine, sarcosine (monomethylglycine) and trimethylamine N-oxide (TMANO) (all from Sigma Chemical Company) were evaluated for their ability to eliminate stops in a dideoxy DNA sequencing method, as described in Example 1. DNA sequencing was otherwise performed as described in example 1. TMANO proved to eliminate stops better than betaine, while dimethylglycine was somewhat less effective. Sarcosine had a measurable effect and is less preferred than the other compounds. Two other N-substituted charged compounds, tetraethylammonium chloride (TEACl) and tetraethylammonium acetate (TEAAc) were also tested. TEACl inhibits the DNA polymerase. TEAAc did not inhibit the DNA polymerase as much as TEACl but also did not reduce the number of stops observed in the sequencing gel.

Example 7
Concentration Ranges of Betaine, TMANO, Sarcosine, and Dimethylglycine Effective in Reducing Stops in a Dideoxy Method of DNA Synthesis The concentration ranges of TMANO, sarcosine, dimethylglycine and betaine were determined according to the procedure described in Example 1.

The results are summarized in the following table.

| Compound | Measurable Effect | Maximal Effect |
|---|---|---|
| betaine | 0.5 M | 2 M |
| TMANO | 0.25 M | 0.5 M |
| Dimethylglycine | 0.5 M | 1.5 M |
| Sarcosine | 0.5 M | 1.5 M |

Example 8
Increasing the Maximum Size of PCR Amplification Products

Betaine was shown to extend the maximum distance between primers for chain elongation in PCR. PCR was performed on T7 DNA as described in B. Krummel, Ph.D. Thesis, University of California, Berkeley, 1990. Approximately 50 pmole of each primer were combined with 2.5 Units of AmpliTaq Polymerase (Perkin-Elmer, Norwalk, Conn., USA) and 0.5 $\mu$g of phage T7 DNA in a 200 $\mu$l reaction containing final concentrations of 200 $\mu$M dNTP, 50 mM KCl, 10 mM Tris-Cl pH8.3, 2.5 mM $MgCl_2$ and 0.01% gelatin. Following a 1' hot start at 94° C., 25 cycles of PCR were performed with cycle times of 90" at 94° C., 1' at 37° C., and 20' at 72° C. The products were precipitated, run on a 1% agarose gel and visualized with UV following ethidium staining.

The addition of betaine at a concentration of 2M allowed two primers which were separated by approximately 4000 base pairs to amplify the intervening DNA region. This DNA region was not appreciably amplified in the absence of betaine.

Example 9
PCR Amplification of Regions Containing Problematic DNA Sequences

Betaine was shown to allow PCR chain elongation through GC-rich DNA regions which have impeded chain elongation in the absence of betaine. PCR was performed on a plasmid containing multiple repeats of the sequence TGC, which we have shown to impede the progress of DNA polymerases (see Example 1, herein). Although the primers were only 500 base pairs apart, a distance which can normally be easily amplified by PCR, the standard reaction conditions failed to produce any amplified product. When betaine was added to a concentration of 2M, the intervening region was amplified.

It is understood that the examples and embodiments described herein are for illustrative purposes only and that various modifications or changes in light thereof will be suggested to persons skilled in the art and are to be included within the spirit and preview of this application and scope of the appended claims. All publications, patents, and patent applications cited herein are hereby incorporated by reference.

What is claimed is:

1. A method of decreasing the incidence of DNA polymerase stops occurring in a reaction mixture containing a DNA polymerase comprising adding to the reaction mixture an amount of a composition of the formula:

(I)

wherein:

$R^1$, $R^2$, and $R^3$ may be the same or different and are independently selected from the group consisting of hydrogen, methyl, ethyl, and propyl, with the proviso that no more than two of $R^1$, $R^2$, and $R^3$ are hydrogen; and X is a moiety selected from the group consisting of:
radicals of the formulas
(a) =O; and (b)

wherein:

$R^4$ is selected from the group consisting of methyl and hydrogen and, when combined with $R^1$, forms a pyrrolidine ring;

$R^5$ is selected from the group consisting of —$CO_2H$ and —$SO_3H$; and n is an integer of from 0 to 2;

with the proviso that, when $R^1$ and $R^4$ form a pyrrolidine ring, no more than one of $R^2$ and $R^3$ is hydrogen, and wherein the composition is added in an amount effective to decrease the incidence of DNA polymerase stops.

2. The method of claim 1 wherein $R^1$, $R^2$ and $R^3$ are the same or different and selected from the group consisting of methyl, ethyl and hydrogen with the proviso that no more than two of $R^1$, $R^2$ and $R^3$ are hydrogen and, when $R^1$ and $R^4$ form a pyrrolidine ring, no more than one of $R^2$ and $R^3$ is hydrogen.

3. The method of claim 2 wherein X is —$CH_2CO_2H$.

4. The method of claim 3 wherein $R^1$, $R^2$ and $R^3$ are methyl.

5. The method of claim 3 wherein $R^1$, $R^2$ are methyl and $R^3$ is hydrogen.

6. The method of claim 3 wherein $R^1$ is methyl and $R^2$ and $R^3$ are hydrogen.

7. The method of claim 2 wherein X is =O.

8. The method of claim 7 wherein $R^1$, $R^2$ and $R^3$ are methyl.

9. The method of claim 2 wherein $R^1$ and $R^4$ form a pyrrolidine ring, $R^2$ and $R^3$ are methyl, n is 0, and $R^5$ is —$CO_2H$.

10. The method of claim 2 wherein $R^1$, $R^2$, and $R^3$ are methyl and X is —$CH_2SO_3H$.

11. The method of claim 1 wherein said reaction mixture is a reaction mixture for a chain termination method of DNA sequencing.

12. The method of claim 11 wherein said chain termination method of DNA sequencing is a dideoxy DNA sequencing method.

13. The method of claim 1 wherein said reaction mixture is a PCR reaction mixture.

14. The method of claim 1 wherein said reaction mixture comprises unpurified DNA.

15. The method of claim 14 wherein said unpurified DNA is a crude cell lysate.

16. A method of decreasing the incidence of DNA polymerase stops in a chain termination DNA sequencing method comprising the steps of:
   a) combining in an aqueous solution, a DNA molecule; a DNA polymerase capable of producing a nucleic acid complementary to a portion of said DNA molecule by using the DNA molecule as a template; a mixture of deoxyribonucledside triphosphates; a chain elongation inhibitor; and an amount of a composition of the formula:

(I)

wherein:
   $R^1$, $R^2$, and $R^3$ may be the same or different and are independently selected from the group consisting of hydrogen, methyl, ethyl, and propyl, with the proviso that no more than two of $R^1$, $R^2$, and $R^3$ are hydrogen; and
   X is a moiety selected from the group consisting of:
      radicals of the formulas
      (a) =O; and (b)

wherein:
   $R^4$ is selected from the group consisting of methyl and hydrogen and, when combined with $R^1$, forms a pyrrolidine ring;
   $R^5$ is selected from the group consisting of —$CO_2H$ and —$SO_3H$; and
   n is an integer of from 0 to 2;
with the proviso that, when $R^1$ and $R^4$ form a pyrrolidine ring, no more than one of $R^2$ and $R^3$ is hydrogen, and wherein the composition is added in an amount effective to decrease the incidence of DNA polymerase stops, to form a reaction mixture; and
   b) incubating the reaction mixture to permit the DNA polymerase to form nucleic acid fragments of varying length by using the DNA molecule as a template, wherein said nucleic acid fragments are complementary to said DNA molecule.

17. The method of claim 16 wherein said chain elongation inhibitors are 2', 3'-dideoxyribonucleoside triphosphates.

18. The method of claim 16 wherein $R^1$, $R^2$ and $R^3$ are the same or different and selected from the group consisting of methyl, ethyl and hydrogen with the proviso that no more two of $R^1$, $R^2$ and $R^3$ are hydrogen and, when $R^1$ and $R^4$ form a pyrrolidine ring, no more than one of $R^2$ and $R^3$ is hydrogen.

19. The method of claim 18 wherein X is —$CH_2CO_2H$.

20. The method of claim 19 wherein $R^1$, $R^2$ and $R^3$ are methyl.

21. The method of claim 19 wherein $R^1$ and $R^2$ are methyl and $R^3$ is hydrogen.

22. The method of claim 19 wherein $R^1$ is methyl and $R^2$ and $R^3$ are hydrogen.

23. The method of 18 wherein X is =O.

24. The method of claim 23 wherein $R^1$, $R^2$ and $R^3$ are methyl.

25. The method of claim 18 wherein $R^1$ and $R^4$ form a pyrrolidine ring, $R^2$ and $R^3$ are methyl, n is 0, and $R^5$ is —$CO_2H$.

26. The method of claim 18 wherein $R^1$, $R^2$, and $R^3$ are methyl and X is —$CH_2SO_3H$.

27. The method of claim 16 wherein said DNA molecule is unpurified DNA.

28. The method of claim 27 wherein said unpurified DNA is a crude cell lysate.

29. The method of claim 16 wherein step a) further comprises the addition of a primer complementary to a second portion of said DNA molecule, said second portion of the DNA molecule located downstream to said first portion of the DNA molecule, wherein said DNA polymerase is capable of extending the 3' end of said primer to produce a nucleic acid complementary to said first portion of the DNA molecule.

30. A kit for sequencing DNA by a chain termination method comprising a container which contains one or more deoxyribonucleoside triphosphates, a container which contains a chain elongation inhibitor, and an amount of a composition of the formula:

(I)

wherein:
   $R^1$, $R^2$, and $R^3$ may be the same or different and are independently selected from the group consisting of hydrogen, methyl, ethyl, and propyl, with the proviso that no more than two of $R^1$, $R^2$, and $R^3$ are hydrogen; and
   X is a moiety selected from the group consisting of:
      radicals of the formulas
      (a) =O; and (b)

wherein:
   $R^4$ is selected from the group consisting of methyl and hydrogen and, when combined with $R^1$, forms a pyrrolidine ring;
   $R^5$ is selected from the group consisting of —$CO_2H$ and —$SO_3H$; and
   n is an integer of from 0 to 2;
with the proviso that, when $R^1$ and $R^4$ form a pyrrolidine ring, no more than one of $R^2$ and $R^3$ is hydrogen.

31. The kit of claim 30 wherein $R^1$, $R^2$ and $R^3$ are the same or different and selected from the group consisting of methyl, ethyl and hydrogen with the proviso that no more two of $R^1$, $R^2$ and $R^3$ are hydrogen and, when $R^1$ and $R^4$ form a pyrrolidine ring, no more than one of $R^2$ and $R^3$ is hydrogen.

32. The kit of claim 31 wherein X is —$CH_2CO_2H$.

33. The kit of claim 32 wherein $R^1$ and $R^2$ are methyl and $R^3$ is hydrogen.

34. The kit of claim 32 wherein $R^1$ is methyl and $R^2$ and $R^3$ are hydrogen.

35. The kit of claim 32 wherein $R^1$, $R^2$ and $R^3$ are methyl.

36. The kit of claim 31 wherein X is =O.

37. The kit of claim 36 wherein $R^1$, $R^2$ and $R^3$ are methyl.

38. The kit of claim 31 wherein $R^1$ and $R^4$ form a pyrrolidine ring, $R^2$ and $R^3$ are methyl, n is 0, and $R^5$ is —$CO_2H$.

39. The kit of claim 31 wherein $R^1$, $R^2$, and $R^3$ are methyl and X is —$CH_2$—$SO_3H$.

40. The kit of claim 30 further comprising an amount of a DNA polymerase enzyme.

41. In the procedure for amplifying a target nucleotide sequence containing trinucleotide repeats, the improvement comprising adding an effective amount of a trimethylglycine to the reaction mixture of a Taq polymerase chain reaction procedure wherein fewer amplification products which do not correspond to the target nucleotide sequence are produced than would be produced in the absence of trimethylglycine.

42. The procedure of claim 41 wherein the nucleotide sequence being amplified is indicative of a disease state.

43. The procedure of claim 41 wherein the target nucleotide sequence is a DNA.

44. A kit for amplifying a target nucleotide sequence containing trinucleotide repeats, comprising in separate containers:
a) the components for a Taq polymerase chain reaction; and
b) a trimethylglycine.

45. The kit of claim 44 wherein the nucleotide sequence being amplified is indicative of a disease state.

46. The kit of claim 44 wherein the target nucleotide sequence is a DNA.

47. A method of claim 1 wherein the reaction mixture comprises an infectious DNA.

48. A method of claim 1 wherein the reaction mixture comprises a DNA molecule having trinucleotide repeats where the trinucleotides are GC rich.

49. A method of claim 13 wherein the composition is trimethylglycine.

50. A kit for inhibiting stops during DNA polymerization comprising:
a. a DNA polymerase; and
b. a composition of the formula:

wherein:

$R^1$, $R^2$, and $R^3$ may be the same or different and are independently selected from the group consisting of hydrogen, methyl, ethyl, and propyl, with the proviso that no more than two of $R^1$, $R^2$, and $R^3$ are hydrogen; and X is a moiety selected from the group consisting of:
radicals of the formulas
(a) =O; and wherein:

$R^4$ is selected from the group consisting of methyl and hydrogen and, when combined with $R^1$, forms a pyrrolidine ring;

$R^5$ is selected from the group consisting of —$CO_2H$ and —$SO_3H$; and n is an integer of from 0 to 2;

with the proviso that, when $R^1$ and $R^4$ form a pyrrolidine ring, no more than one of $R^2$ and $R^3$ is hydrogen.

51. A kit of claim 50 wherein the composition is trimethylglycine.

52. A kit of claim 50 wherein the kit comprises Taq polymerase.

53. A kit of claim 50 wherein the kit further comprises components specific for polymerase chain reaction.

54. A method to reduce premature chain termination in the replication of a DNA molecule from a template DNA molecule, the method comprising the steps of:

adding to a reaction mixture of the DNA template and a DNA polymerase an effective amount of chain termination reducing compound selected from the group consisting of trimethylglycine (betaine) and trimethylamine N-oxide (TMANO) so as to reduce premature chain termination which would otherwise occur in the absence of the chain termination reducing compound.

55. A method to reduce premature chain termination in the replication of a DNA molecule from a template DNA molecule, the method comprising the steps of:

adding to a reaction mixture of the DNA template and a DNA polymerase an effective amount of trimethylglycine (betaine) so as to reduce premature chain termination which would otherwise occur in the absence of the trimethylglycine (betaine).

56. An improvement to methods for replication of a DNA molecule using a template DNA molecule, the improvement reducing premature chain termination, the improvement comprising the step of adding to a reaction mixture of the DNA template and a DNA polymerase an effective amount of a chain termination reducing compound selected from the group consisting of trimethylglycine (betaine) and trimethylamine N-oxide (TMANO) so as to reduce premature chain termination which would otherwise occur in the absence of the chain termination reducing compound.

57. An improvement to methods for replication of a DNA molecule using a template DNA molecule, the improvement reducing premature chain termination, the improvement comprising the step of adding to a reaction mixture of the DNA template and a DNA polymerase an effective amount of trimethylglycine (betaine) so as to reduce premature chain termination which would otherwise occur in the absence of the trimethylglycine (betaine).

58. In the procedure for replicating a template nucleotide sequence containing trinucleotide repeats inhibitory to chain elongation, the improvement comprising adding an effective amount of a trimethylglycine to the reaction mixture of a Taq polymerase DNA replication reaction procedure wherein fewer different replication products which do not correspond to the template nucleotide sequence are produced than would be produced in the absence of trimethylglycine.

59. A kit for replicating a target nucleotide sequence comprising:

(a) a DNA polymerase; and (b) a trimethylglycine.

60. A kit for replicating a target nucleotide sequence containing trinucleotide repeats inhibitory to chain elongation, comprising:

(a) the components for a Taq polymerase DNA replication procedure; and (b) a trimethylglycine.

61. In the procedure for sequencing a target nucleotide sequence containing trinucleotide repeats, the improvement comprising adding an effective amount of a trimethylglycine to the reaction mixture of a sequencing procedure wherein fewer sequencing products which do not correspond to the target nucleotide sequence are produced than would be produced in the absence of trimethylglycine.

62. The procedure of claim 1 wherein the target nucleotide sequence is DNA.

63. The procedure of claim 1 wherein the sequencing procedure is enzymatic sequencing.

* * * * *